(12) United States Patent
Fujimori et al.

(10) Patent No.: US 10,188,269 B2
(45) Date of Patent: Jan. 29, 2019

(54) MANUFACTURING METHOD FOR IMAGE PICKUP UNIT AND IMAGE PICKUP UNIT

(71) Applicant: OLYMPUS CORPORATION, Tokyo (JP)

(72) Inventors: Noriyuki Fujimori, Suwa (JP); Kazuaki Kojima, Suwa (JP)

(73) Assignee: OLYMPUS CORPORATION, Tokyo (JP)

( * ) Notice: Subject to any disclaimer, the term of this patent is extended or adjusted under 35 U.S.C. 154(b) by 0 days.

(21) Appl. No.: 15/591,778

(22) Filed: May 10, 2017

(65) Prior Publication Data

US 2017/0238785 A1   Aug. 24, 2017

Related U.S. Application Data

(60) Division of application No. 14/456,560, filed on Aug. 11, 2014, now Pat. No. 9,681,067, which is a (Continued)

(30) Foreign Application Priority Data

Oct. 8, 2008 (JP) .................................. 2008-262070
Oct. 10, 2008 (JP) .................................. 2008-264503

(51) Int. Cl.
*H01L 27/146* (2006.01)
*A61B 1/00* (2006.01)
(Continued)

(52) U.S. Cl.
CPC ........ *A61B 1/0011* (2013.01); *A61B 1/00096* (2013.01); *A61B 1/00163* (2013.01); (Continued)

(58) Field of Classification Search
CPC ......... H01L 27/14687; H01L 27/14632; H01L 27/1469; H01L 27/14636; H01L 21/78; H01L 24/94
See application file for complete search history.

(56) References Cited

U.S. PATENT DOCUMENTS 4,692,608 A   9/1987  Cooper et al.
5,371,384 A   12/1994 Wada
(Continued)

FOREIGN PATENT DOCUMENTS

JP   HE1-7-24088      6/1995
JP   10-319297 A     12/1998
(Continued)

OTHER PUBLICATIONS

United States Office Action dated Mar. 7, 2012 received in related U.S. Appl. No. 12/574,157.
(Continued)

*Primary Examiner* — Thanh Luu
(74) *Attorney, Agent, or Firm* — Scully, Scott, Murphy & Presser, P.C.

(57) ABSTRACT

A manufacturing method for an image pickup unit, the method including: a step of bonding plural lens wafers, on which optical components are formed, and forming a lens unit wafer including plural lens units; a step of bonding a bending optical element wafer including plural bending optical elements to a first surface of the lens unit wafer such that the plural bending optical elements are respectively opposed to the plural lens units and forming an optical unit wafer; a step of separating and individualizing the optical unit wafer for each of the lens units and the bending optical elements and manufacturing plural optical units; and a step (Continued)

of respectively bonding solid-state image pickup devices to emission surfaces of lights of the bending optical elements of the optical units.

4 Claims, 16 Drawing Sheets

Related U.S. Application Data continuation of application No. 12/574,157, filed on Oct. 6, 2009, now Pat. No. 8,823,859.

(51) Int. Cl.
| | |
|---|---|
| *A61B 1/05* | (2006.01) |
| *G02B 7/02* | (2006.01) |
| *G02B 13/00* | (2006.01) |
| *G02B 23/24* | (2006.01) |
| *H04N 5/225* | (2006.01) |
| *B32B 37/14* | (2006.01) |
| *B32B 38/10* | (2006.01) |
| *H04N 5/335* | (2011.01) |

(52) U.S. Cl.
CPC ............. *A61B 1/051* (2013.01); *B32B 37/14* (2013.01); *B32B 38/10* (2013.01); *G02B 7/02* (2013.01); *G02B 13/006* (2013.01); *G02B 13/007* (2013.01); *G02B 13/0035* (2013.01); *G02B 13/0065* (2013.01); *G02B 13/0085* (2013.01); *G02B 23/243* (2013.01); *H01L 27/14643* (2013.01); *H01L 27/14687* (2013.01); *H04N 5/2254* (2013.01); *H04N 5/335* (2013.01); *Y10T 156/1052* (2015.01)

(56) References Cited

U.S. PATENT DOCUMENTS

| | | | |
|---|---|---|---|
| 6,476,851 B1 | 11/2002 | Nakamura | |
| 6,828,542 B2 | 12/2004 | Ye et al. | |
| 7,242,027 B2 | 7/2007 | Schranz | |
| 7,787,939 B2 | 8/2010 | Jacobsen et al. | |
| 2004/0047274 A1* | 3/2004 | Amanai | G02B 7/022 369/125 |
| 2004/0225189 A1 | 11/2004 | Kimoto et al. | |
| 2005/0124858 A1 | 6/2005 | Matsuzawa et al. | |
| 2006/0023990 A1 | 2/2006 | Shih et al. | |
| 2006/0193214 A1 | 8/2006 | Shimano et al. | |
| 2006/0232668 A1 | 10/2006 | Horn et al. | |
| 2006/0258901 A1 | 11/2006 | Fujimori et al. | |
| 2007/0166029 A1 | 7/2007 | Lee et al. | |
| 2009/0206431 A1* | 8/2009 | Bolken | G02B 7/02 257/432 |
| 2009/0244259 A1 | 10/2009 | Kojima et al. | |

FOREIGN PATENT DOCUMENTS

| | | |
|---|---|---|
| JP | 2004-29554 A | 1/2004 |
| JP | 2005-539276 A | 12/2005 |
| JP | 2006-236516 A | 9/2006 |
| JP | 2007-068894 A | 3/2007 |
| WO | 2004/027880 A2 | 4/2004 |
| WO | 2008/118085 A2 | 10/2008 |

OTHER PUBLICATIONS

United States Office Action dated Jul. 24, 2012 received in related U.S. Appl. No. 12/574,157.
United States Office Action dated Feb. 21, 2013 received in related U.S. Appl. No. 12/574,157.
United States Office Action dated Sep. 9, 2013 received in related U.S. Appl. No. 12/574,157.
United States Office Action dated Sep. 15, 2016 received in related U.S. Appl. No. 14/456,560.
United States Office Action dated Apr. 25, 2016 received in related U.S. Appl. No. 14/456,560.

* cited by examiner

MANUFACTURING METHOD FOR IMAGE PICKUP UNIT AND IMAGE PICKUP UNIT

CROSS REFERENCE TO RELATED APPLICATION

This application is a divisional application of U.S. patent application Ser. No. 14/456,560 filed on Aug. 11, 2014, which is a continuation application of U.S. patent application Ser. No. 12/574,157 filed on Oct. 6, 2009, now U.S. Pat. No. 8,823,859 B2, which claims the benefit of Japanese Patent Application No. 2008-262070 filed in Japan on Oct. 8, 2008 and Japanese Patent Application No. 2008-264503 filed in Japan on Oct. 10, 2008, the entire contents of each of which are incorporated herein by reference.

BACKGROUND OF THE INVENTION

1. Field of the Invention

The present invention relates to an image pickup unit, an optical unit, and a manufacturing method for the image pickup unit.

2. Description of the Related Art

An electronic endoscope, a cellular phone with camera, a digital camera, and the like including an image pickup unit provided with a solid-state image pickup device such as a CCD or a CMOS are being widely spread.

A main section of the image pickup unit includes the solid-state image pickup device and an optical unit including a lens for making an optical image of a subject incident on a light receiving section of the solid-state image pickup device. In the cellular phone with camera and the digital camera reduced in size and thickness or the electronic endoscope adapted to view sideways and reduced in diameter of an insertion section, for the purpose of, for example, bending an optical axis or realizing a reduction in thickness of the image pickup unit, the optical unit further includes a bending optical element such as a prism. The image pickup unit in which the optical unit includes the bending optical element is disclosed in, for example, Japanese Utility Model Laid-Open No. Hei 7-24088.

As shown in FIG. 1, a main section of an image pickup unit 65 disclosed in Japanese Utility Model Laid-Open No. Hei 7-24088 includes an optical unit 68 and a solid-state image pickup device 64. A main section of the optical unit 68 includes a lens unit 62 and a prism 63. A main section of the lens unit 62 includes a lens barrel 62c, a first lens unit 62a and a second lens unit 62b including plural lenses provided in the lens barrel 62c, and a coupling frame 62d fit in an outer circumference on a rear end side in an optical axis direction of the lens barrel 62c.

An incident surface 63a of the prism 63 is bonded and fixed to a rear end in the optical axis direction of the coupling frame 62d. The solid-state image pickup device 64 is fixed to an emission surface 63c of the prism 63.

In the image pickup unit 65 having such a configuration, adjustment of an angle of deviation and centering of an optical system in the optical unit 68 can be realized by alignment adjustment of the two lens units 62a and 62b, the prism 63, and the solid-state image pickup device 64.

However, in the image pickup unit disclosed in Japanese Utility Model Laid-Open No. Hei 7-24088, when the optical unit 68 and the image pickup unit 65 are manufactured, after the prism 63 and the lens unit 62 are separately formed, the prism 63 is bonded to a rear end portion of the coupling frame 62d of the lens unit 62. Since work for adjusting the angle of deviation and the centering of the optical system in the optical unit 68 is difficult and takes long time, the work causes an increase in cost. There is a demand for a manufacturing method that can manufacture a large number of optical units and image pickup units at a time at low cost.

On the other hand, a main section of the image pickup unit includes the solid-state image pickup device and an optical unit including a lens for making an optical image of a subject incident on a light receiving section of the solid-state image pickup device. In recent years, as the optical unit, an optical unit in which optical components are laminated in plural layers is well known. The optical unit is formed by slicing an optical unit wafer after bonding plural lens wafers, which form the optical components such as a lens, a stop, and a spacer, and forming the optical unit wafer.

As the image pickup unit, an image pickup unit is well known which is formed by slicing an image pickup unit wafer after bonding plural lens wafers, which form the optical components such as a lens, a stop, and a spacer, and forming an optical unit wafer and further bonding a sensor wafer including a solid-state image pickup device to the optical unit wafer and forming the image pickup unit wafer.

For example, Japanese Patent Application Laid-Open Publication No. 2004-29554 discloses an image pickup unit 224 formed by, as shown in FIG. 2, bonding an image pickup device 223 to a bottom surface of an optical unit 222 formed by laminating lenses 222a to 222c as optical components in plural layers to have spaces in an optical axis direction in a part between the lenses 222a and 222b and between the lenses 222b and 222c.

In the optical unit 222 shown in FIG. 2, the optical unit 222 is formed by cutting an optical unit wafer by dicing or the like after bonding a lens wafer including the lens 222a, a lens wafer including the lens 222b, and a lens wafer including the lens 222c and forming the optical unit wafer. As an external shape of the optical unit 222, as shown in FIG. 2, a planar shape viewed from above is often a square shape or a polygonal shape because of a limitation in a processing method.

In the optical unit 222 disclosed in Japanese Patent Application Laid-Open Publication No. 2004-29554, an area functioning as an optical lens, i.e., an area functioning to focus an optical image of a subject on the image pickup device 223 in the optical unit 222, in other words, an area through which a light beam from the subject passes is set to a dimension equal to or smaller than a dimension of a circle C inscribed in a square forming an external shape of the optical unit 222 as shown in FIG. 2 in a state of plan view from above.

Therefore, as explained above, since the external shape of the optical unit 222 is formed in the square shape or the like because of the limitation in the processing method, as shown in FIG. 2, an area D as an outer circumferential area of the circle C is an optically ineffective area in the state of plan view from above. Therefore, a useless area is formed in the optical unit 222.

As shown in FIGS. 3 and 4, in general, in an insertion section distal end 231 of an endoscope, besides an image pickup unit 234, a light guide 235 for illumination, a treatment instrument inserting-through channel 236, and the like are provided around the image pickup unit 234. As shown in FIG. 4, an external dimension of the insertion section distal end 231 of the endoscope is determined by an external shape of the image pickup unit 234 itself and an external shape of the light guide 235 for illumination and the treatment instrument inserting-through channel 236. However, even in this case, if an optically ineffective area E is formed in the image pickup unit 234, the external shape of the image pickup unit 234 is increased in size. Therefore, the insertion section distal end 231 of the endoscope is increased in diameter. This may be a cause of pain for a patient.

SUMMARY OF THE INVENTION

A manufacturing method for an image pickup unit according to a first embodiment of the present invention, the method comprising: a step of bonding plural lens wafers, on which optical components are formed, and forming a lens unit wafer including plural lens units; a step of bonding a bending optical element wafer including plural bending optical elements to a first surface of the lens unit wafer such that the plural bending optical elements are respectively opposed to the plural lens units and forming an optical unit wafer; a step of separating and individualizing the optical unit wafer for each of the lens units and the bending optical elements and manufacturing plural optical units; and a step of respectively bonding solid-state image pickup devices to emission surfaces of lights of the bending optical elements of the optical units.

An image pickup unit according to a second embodiment of the present invention, the image pickup unit being manufactured with the manufacturing method according to the first embodiment of the present invention.

DETAILED DESCRIPTION OF THE PREFERRED EMBODIMENTS

Embodiments of the present invention are explained below with reference to the accompanying drawings.

First Embodiment

Figure 1:
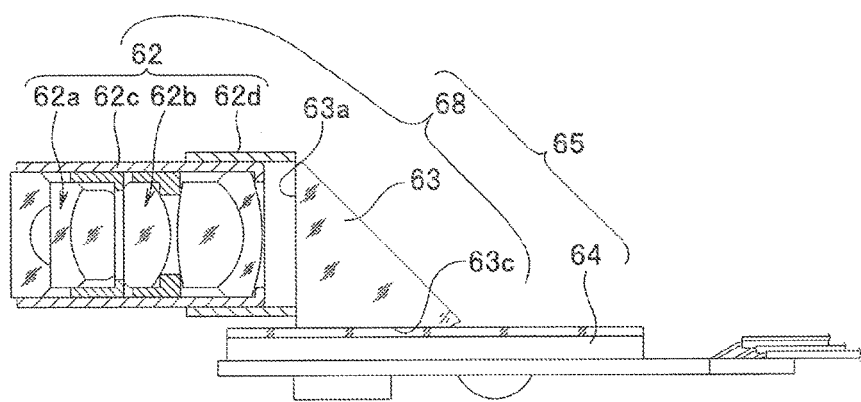
FIG. 1 is a schematic partial sectional view of a configuration of a conventional image pickup unit.
Figure 2:
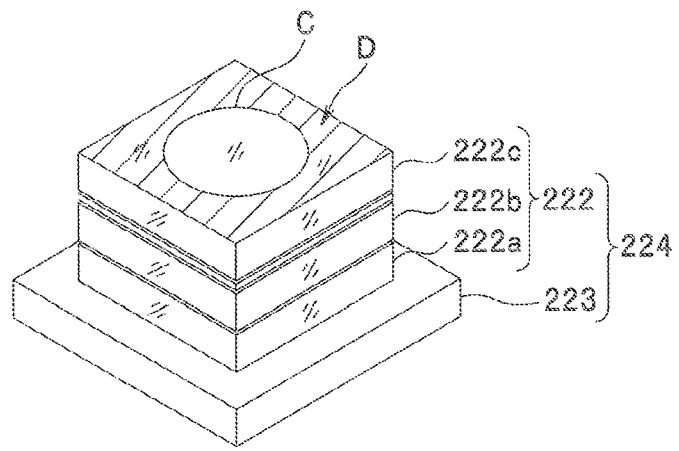
FIG. 2 is a schematic perspective view of the configuration of the conventional image pickup unit.
Figure 3:
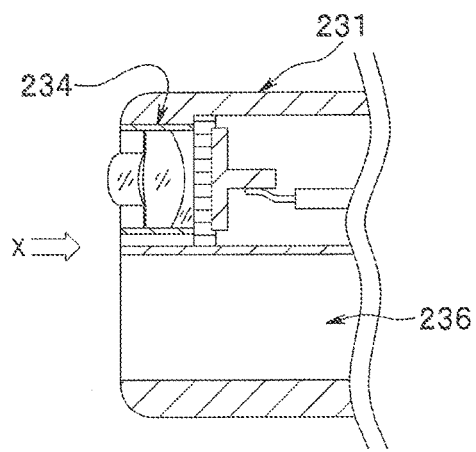
FIG. 3 is a schematic partial sectional view of a configuration of an insertion section distal end side in a state in which the conventional image pickup unit is provided at a distal end of an insertion section of an endoscope.
Figure 4:
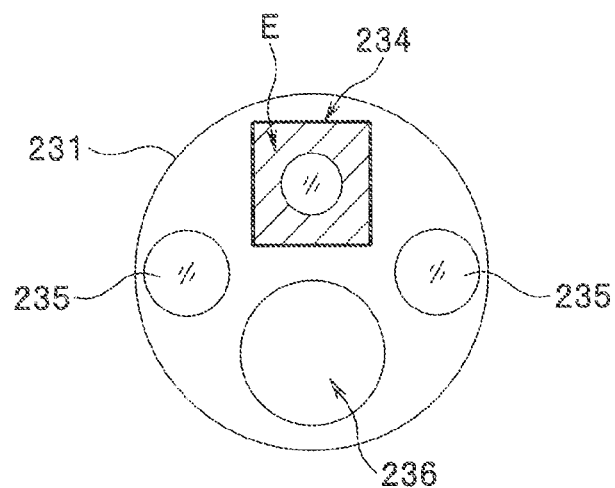
FIG. 4 is a plan view of FIG. 3 viewed from an X direction.
Figure 5:
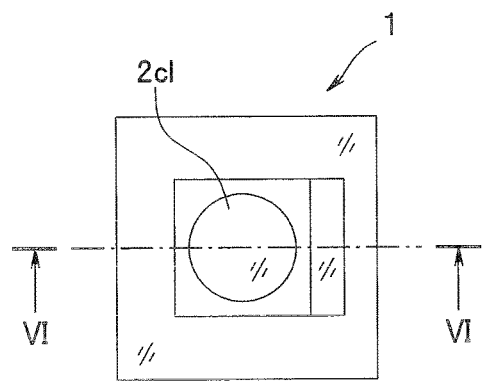
FIG. 5 is a top view of an optical unit according to a first embodiment of the present invention.
Figure 6:
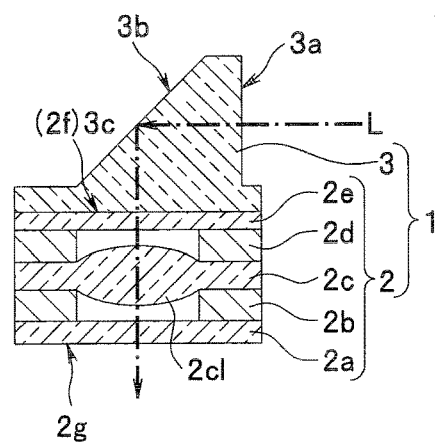
FIG. 6 is a sectional view of the optical unit taken along VI-VI line in FIG. 5.

First, a configuration of an optical unit manufactured by a manufacturing method for an optical unit according to a first embodiment of the present invention is explained with reference to FIGS. 5 and 6. As shown in FIGS. 5 and 6, a main section of an optical unit 1 includes a lens unit 2 and a bending optical element 3.

The lens unit 2 forms an optical image emitted from the bending optical element 3 on a solid-state image pickup device 4 (see FIG. 9) explained later. A main section of the lens unit 2 includes a flat plate 2a formed of a transparent member, a spacer 2b superimposed on the flat plate 2a and having a through hole formed in an optical path of light beam L of the optical image, a lens member 2c superimposed on the spacer 2b and having a convex convex lens 2c1 located in the optical path of the light beam L, a stop 2d superimposed on the lens member 2c and having a through hole formed in the optical path of the light beam L, and a flat plate 2e superimposed on the stop 2d and formed of a transparent member. In other words, the lens unit 2 is formed by laminating the plural optical members (2a to 2e). The lens unit 2 may include not only one convex convex lens 2c1 but also plural lenses.

A first surface 2f of the lens unit 2 forms an incident surface of the light beam L on the lens unit 2. A second surface 2g opposed to the first surface 2f of the lens unit 2 forms an emission surface of the light beam L from the lens unit 2. The stop 2d may be located between the flat plate 2a and the lens member 2c instead of the spacer 2b. The spacer 2b may be located between the lens member 2c and the flat plate 2e instead of the stop 2d. The entire flat plates 2a and 2e do not need to be formed of the transparent members. Only the optical paths of the light beam L have to be formed of the transparent members.

The bending optical element 3 includes, for example, a prism. The bending optical element 3 is provided by bonding the emission surface 3c to an outer surface of the flat plate 2e serving as the first surface 2f of the lens unit 2. The bending optical element 3 may include not only the prism but also a reflecting mirror and the like.

The bending optical element 3 refracts, on an inclined plane 3b, the light beam L of the optical image made incident from an incident surface 3a, i.e., changes a direction of the light beam L on the inclined plane 3b and makes the light beam L incident on the lens unit 2 from the emission surface 3c.

Figure 7:
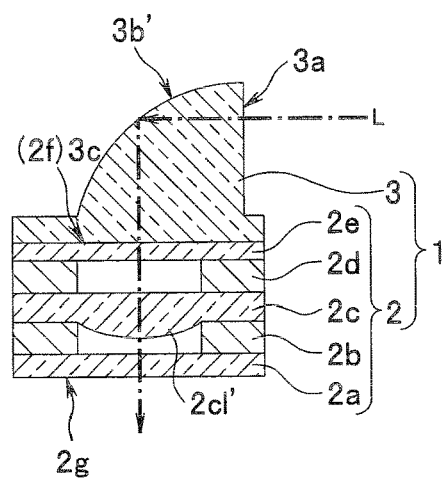
FIG. 7 is a sectional view of a configuration of a modification of the optical unit shown in FIG. 6.

As shown in FIG. 7, the inclined plane 3b may be formed as a curved surface 3b'. In this case, since the curved surface 3b' functions as a convex lens, as shown in FIG. 7, a lens of the lens member 2c of the lens unit 2 may be a plano-convex lens 2c1' rather than the convex convex lens 2c1. Therefore, a material of the lens member 2c can be reduced from that in the configuration shown in FIG. 6.

In the optical unit 1 having such a configuration, incident light beam L from a subject image is made incident on the bending optical element 3 from the incident surface 3a of the bending optical element 3, refracted on the inclined plane 3b or the curved surface 3b', and then emitted from the emission surface 3c. The light beam L emitted from the emission surface 3c is made incident on the lens unit 2 from the first surface 2f of the lens unit 2 and emitted to the solid-state image pickup device 4 explained later from the second surface 2g.

Figure 8:
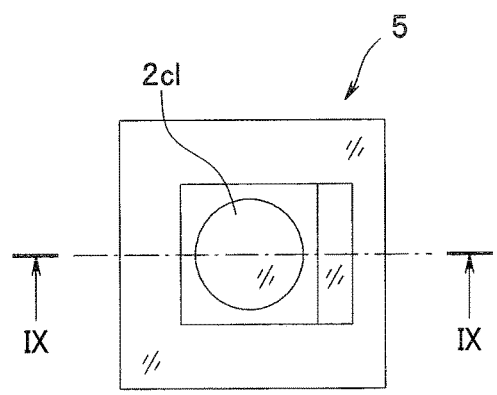
FIG. 8 is a top view of an image pickup unit according to the first embodiment.
Figure 9:
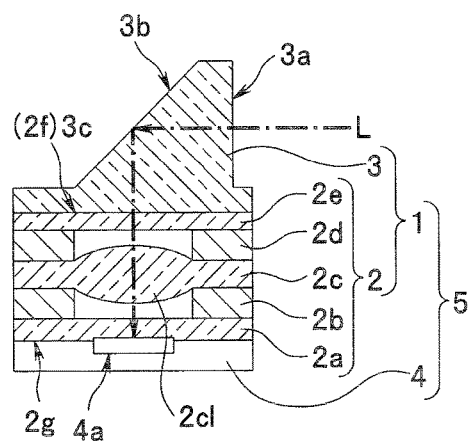
FIG. 9 is a sectional view of the image pickup unit taken along IX-IX line in FIG. 8.

A configuration of an image pickup unit manufactured by a manufacturing method for an image pickup unit according to the present embodiment is explained with reference to FIGS. 8 and 9. As shown in FIGS. 8 and 9, a main section of an image pickup unit 5 includes the optical unit 1 and the solid-state image pickup device 4. A configuration of the optical unit 1 is the same as the configuration shown in FIGS. 5 to 7. Therefore, explanation of the configuration is omitted.

The solid-state image pickup device 4 is provided to be bonded to the second surface 2g of the lens unit 2, specifically, an outer surface of the flat plate 2a in a position where a light receiving section 4a receives the light beam L emitted from the second surface 2g of the lens unit 2.

The solid-state image pickup device 4 receives, in the light receiving section 4a, an optical image formed via the bending optical element 3 and the lens unit 2 and performs exchange of a video signal with an external device via a wire piercing through a not-shown substrate that fixes the solid-state image pickup device 4.

Manufacturing methods for the optical unit 1 and the image pickup unit 5 shown in FIGS. 5 to 9 are explained with reference to FIGS. 10 to 14.

Figure 10:
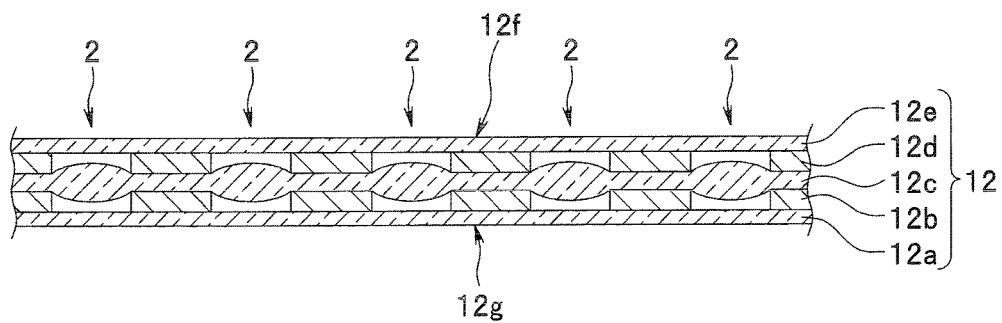
FIG. 10 is a partial sectional view of a lens unit wafer.

First, as shown in FIG. 10, plural lens wafers on which optical components are formed are bonded to form a lens unit wafer 12 including a plurality of the lens units 2. Specifically, first, the lens unit wafer 12 is formed by superimposing and bonding a lens wafer 12b including a plurality of the spacers 2b on a lens wafer 12a including a plurality of the flat plates 2a, superimposing and bonding a lens wafer 12c including a plurality of the lens members 2c on the lens wafer 12b, superimposing and bonding a lens wafer 12d including a plurality of the stops 2d on the lens wafer 12c, and superimposing and bonding a lens wafer 12e including a plurality of the flat plates 2e on the lens wafer 12d. As a result, a plurality of the lens units 2 including the flat plates 2a, the spacers 2b, the lens members 2c, the stops 2d, and the flat plates 2e are formed on the lens unit wafer 12.

The lens wafers 12a to 12d are bonded such that transparent sections of the flat plates 2a and 2e, the through holes of the spacers 2b and the stops 2d, and the convex convex lenses 2c1 of the lens members 2c are respectively located on optical axes of light beams L.

Figure 11:
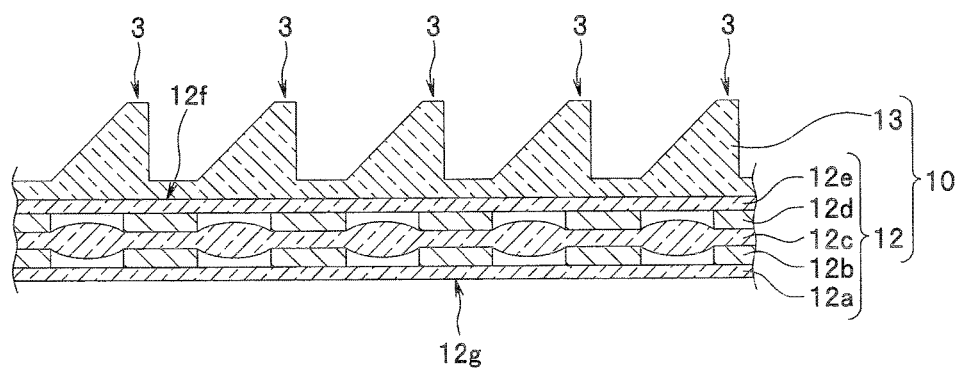
FIG. 11 is a partial sectional view of a state in which a bending optical element wafer is bonded to a first surface of the lens unit wafer shown in FIG. 10 to form an optical unit wafer.

Subsequently, as shown in FIG. 11, a bending optical element wafer 13 including a plurality of the bending optical elements 3 is bonded to the first surface 12f forming an incident surface of the light beam L of the lens unit wafer 12, specifically, an outer surface of the lens wafer 12e such that the bending optical elements 3 are respectively opposed to the lens units 2 and emission surfaces 3c of the bending optical elements 3 are set in contact with the lens units 2. An optical unit wafer 10 including a plurality of the optical units 1 is formed.

In this state, although not shown in the figure, if the optical unit wafer 10 is separated and individualized for each of the lens units 2, i.e., for each of the optical units 1 and the bending optical elements 3, a plurality of the optical units 1 shown in FIGS. 5 and 6 are manufactured.

Figure 12:
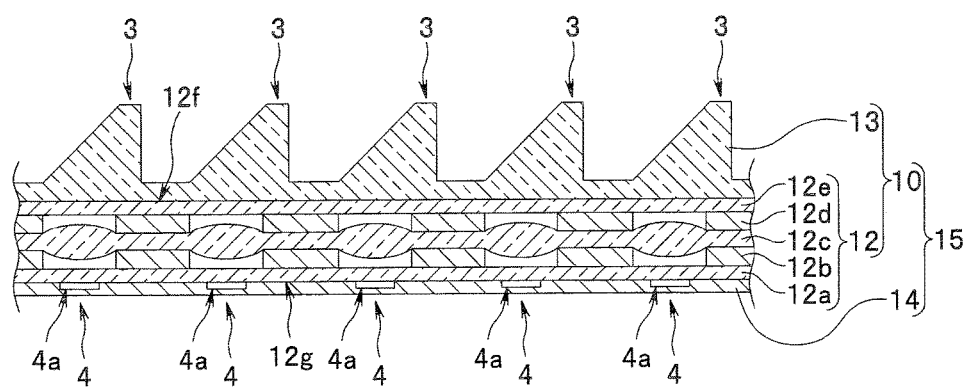
FIG. 12 is a partial sectional view of a state in which a sensor wafer is bonded to a second surface of the lens unit wafer shown in FIG. 11 to form an image pickup unit wafer.

When the image pickup unit 5 is manufactured, as shown in FIG. 12, a sensor wafer 14 including a plurality of the solid-state image pickup devices 4 is bonded to the second surface 12g forming an emission surface of the light beam L opposed to the first surface 12f of the lens unit wafer 12 in the optical unit wafer 10 shown in FIG. 11, specifically, an outer surface of the lens wafer 12a such that the solid-state image pickup devices 4 are respectively opposed to the lens units 2. An image pickup unit wafer 15 including a plurality of the image pickup units 5 including the optical units 1 and the solid-state image pickup devices 4 is formed.

Specifically, as shown in FIG. 12, the sensor wafer 14 is bonded to the second surface 12g of the lens unit wafer 12 in positions where light receiving sections 4a of the solid-state image pickup devices 4 receive the light beams L emitted from the lens units 2.

Figure 13:
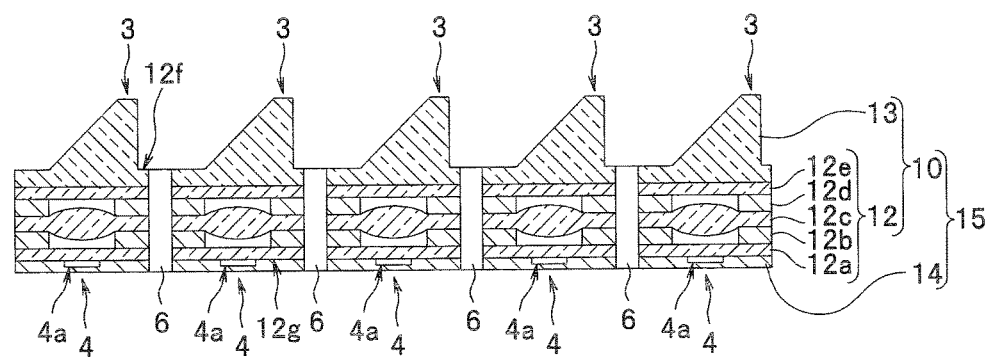
FIG. 13 is a partial sectional view of a state in which dicing lines are formed for respective lens units on the image pickup unit wafer shown in FIG. 12.
Figure 14:
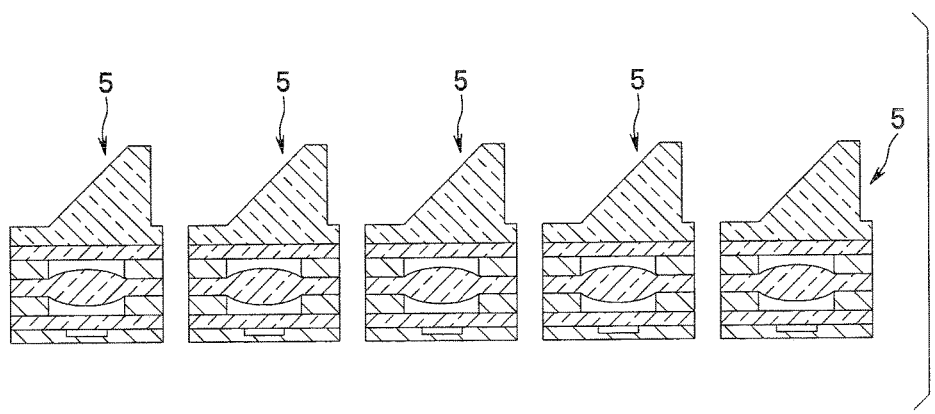
FIG. 14 is a partial sectional view of a state in which plural image pickup units are individualized from the image pickup unit wafer starting from the dicing lines shown in FIG. 13.

Thereafter, as shown in FIG. 13, dicing lines 6 are formed in the image pickup unit wafer 15 respectively for the lens units 2 and the bending optical elements 3 and the solid-state image pickup devices 4, i.e., the image pickup units 5. As shown in FIG. 14, the image pickup unit wafer 15 is separated and individualized on the basis of the dicing lines 6. Then, a plurality of the image pickup units 5 shown in FIGS. 8 and 9 are manufactured.

In this way, in the present embodiment, the plural optical units 1 are manufactured by bonding the plural lens wafers 12a to 12e, on which the optical components are formed, and forming the lens unit wafer 12 including the plural lens unit 2, bonding the bending optical element wafer 13 including the plural bending optical elements 3 to the first surface 12f of the lens unit wafer 12 and forming the optical unit wafer 10, and individualizing the optical unit wafer 10.

The plural image pickup units 5 are manufactured by bonding the sensor wafer 14 including the plural solid-state image pickup devices 4 to the second surface 12g in the lens unit wafer 12 of the optical unit wafer 10 and forming the image pickup unit wafer 15 and individualizing the image pickup unit wafer 15.

Consequently, the optical unit 1 shown in FIGS. 5 and 6 or the image pickup unit 5 shown in FIGS. 8 and 9 is formed at a wafer level. Therefore, focus adjustlessness can be realized by adjusting and managing the thicknesses of the wafers that form the optical units 1 or the image pickup units 5.

Accurate alignment adjustment can be easily performed by using a wafer process. Therefore, work for adjusting an angle of deviation and centering of an optical system in the optical unit 1 is substantially reduced. A large number of optical units 1 or the image pickup units 5 can be collectively manufactured. Consequently, high yield and low cost can be realized.

As explained in a second embodiment of the present invention later, a recess or an opening (both of which are not shown in the figure) is formed in a position opposed to the light receiving section 4a of the solid-state image pickup device 4 on the second surface 2g of the lens unit 2 of the optical unit 1. Then, the image pickup unit 5 can be manufactured without spoiling a microlens effect of the solid-state image pickup device 4.

Consequently, it is possible to provide the manufacturing method for the optical unit 1 and the manufacturing method for the image pickup unit 5 that can reduce work for adjusting an angle of deviation and centering of the optical system in the optical unit 1 and efficiently manufacture the optical unit 1 and the image pickup unit 5 as well as the optical unit 1 and the image pickup unit 5.

Second Embodiment

An optical unit and an image pickup unit according to a second embodiment of the present invention are explained below. Configurations of the optical unit and the image pickup unit according to the present embodiment are different from those of the optical unit and the image pickup unit according to the first embodiment in that a direction of light made incident on the optical unit is opposite and the solid-state image pickup device is bonded to the emission surface of the bending optical element. Therefore, only these differences are explained. Components same as those in the first embodiment are denoted by the same reference numerals and signs and explanation of the components is omitted.

Figure 15:
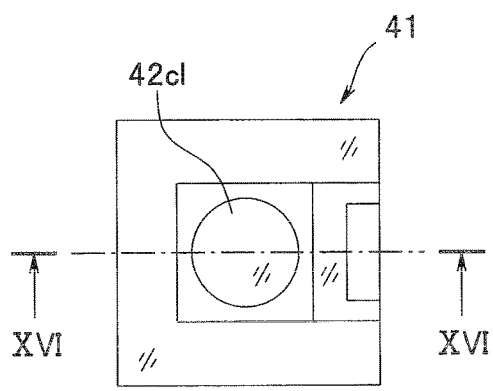
FIG. 15 is a top view of an optical unit according to a second embodiment of the present invention.
Figure 16:
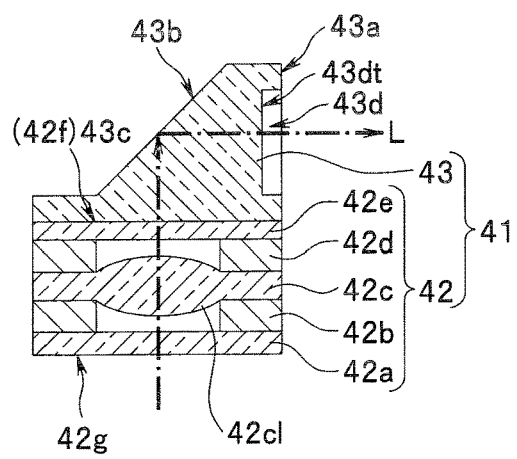
FIG. 16 is a sectional view of the optical unit taken along XVI-XVI line in FIG. 15.

First, a configuration of an optical unit manufactured by a manufacturing method for an optical unit according to the present embodiment is explained with reference to FIGS. 15 and 16. As shown in FIGS. 15 and 16, a main section of an optical unit 41 includes a lens unit 42 and a bending optical element 43.

The lens unit 42 forms an optical image on a solid-state image pickup device 44 (see FIG. 18) explained later via the bending optical element 43. A main section of the lens unit 42 includes a flat plate 42a formed of a transparent member, a spacer 42b superimposed on the flat plate 42a and having a through hole formed in an optical path of light beam L of the optical image, a lens member 42c superimposed on the spacer 42b and having a convex convex lens 42c1 located in the optical path of the light beam L, a stop 42d superimposed on the lens member 42c and having a through hole formed in the optical path of the light beam L, and a flat plate 42e superimposed on the stop 42d and formed of a transparent member. In other words, the lens unit 42 is formed by laminating the plural optical members (42a to 42e). The lens unit 42 may include not only one lens 42c1 but also plural lenses.

A first surface 42f of the lens unit 42 forms an emission surface of the light beam L from the lens unit 42. A second surface 42g opposed to the first surface 42f of the lens unit 42 forms an incident surface of the light beam L on the lens unit 42.

The stop 42d may be located between the flat plate 42a and the lens member 42c instead of the spacer 42b. The spacer 42b may be located between the lens member 42c and the flat plate 42e instead of the stop 42d. The entire flat plates 42a and 42e do not need to be formed of the transparent members. Only the optical paths of the light beam L have to be formed of the transparent members.

The bending optical element 43 includes, for example, a prism. The bending optical element 43 is provided by bonding an incident surface 43c to an outer surface of the flat plate 42e serving as the first surface 42f of the lens unit 42. The bending optical element 43 is may include not only the prism but also a reflecting mirror and the like.

The bending optical element 43 refracts, on an inclined plane 43b, the light beam L of the optical image made incident from the first surface 42f of the lens unit 42, i.e., changes a direction of the light beam L on the inclined plane 43b and makes the light beam L incident on the solid-state image pickup device 44 from an emission surface 43a. The inclined plane 43b may be formed as a curved surface as shown in FIG. 7.

A recess 43d is formed in the emission surface 43a of the bending optical element 43. An optical surface 43dt is formed on a bottom surface of the recess 43d. The light beam L is also emitted from the optical surface 43dt.

In the optical unit 41 having such a configuration, incident light beam L from a subject image is made incident on the lens unit 42 from the second surface 42g, made incident on the bending optical element 43 from the first surface 42f via the incident surface 43c, refracted on the inclined plane 43b, and then emitted from the emission surface 43a. The light beam L emitted from the emission surface 43a is made incident on the solid-state image pickup device 44 explained later.

A configuration of an image pickup unit manufactured by a manufacturing method for an image pickup unit according to the present embodiment is explained with reference to FIGS. 17 and 18.

Figure 17:
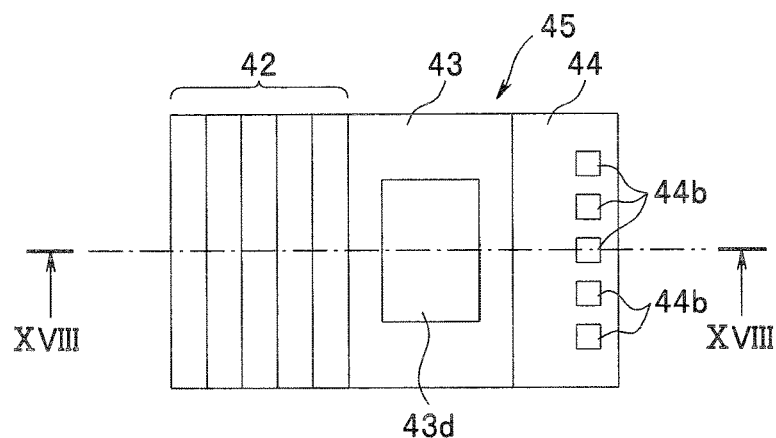
FIG. 17 is a top view of an image pickup unit according to the second embodiment.
Figure 18:
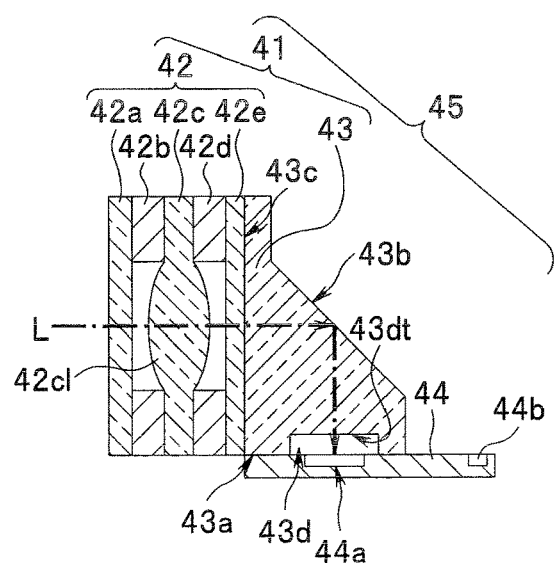
FIG. 18 is a sectional view of the image pickup unit taken along XVIII-XVIII line in FIG. 17.

As shown in FIGS. 17 and 18, a main section of an image pickup unit 45 includes the optical unit 41 and the solid-state image pickup device 44. A configuration of the optical unit 41 is the same as the configuration shown in FIGS. 15 and 16. Therefore, explanation of the configuration is omitted.

The solid-state image pickup device 44 is provided to be bonded to the emission surface 43a of the bending optical element 43 after being aligned in a position where a space is formed between a light receiving section 44a and the optical surface 43dt and the light receiving section 44a receives the light beam L emitted from the optical surface 43dt.

The solid-state image pickup device 44 receives, in the light receiving section 44a, an optical image formed via the lens unit 42 and the bending optical element 43 and performs exchange of a video signal with an external device via a not-shown wire electrically connected to an electrode 44b of the solid-state image pickup device 44.

Manufacturing methods for the optical unit 41 and the image pickup unit 45 shown in FIGS. 15 to 18 are explained with reference to FIGS. 19 to 21.

Figure 19:
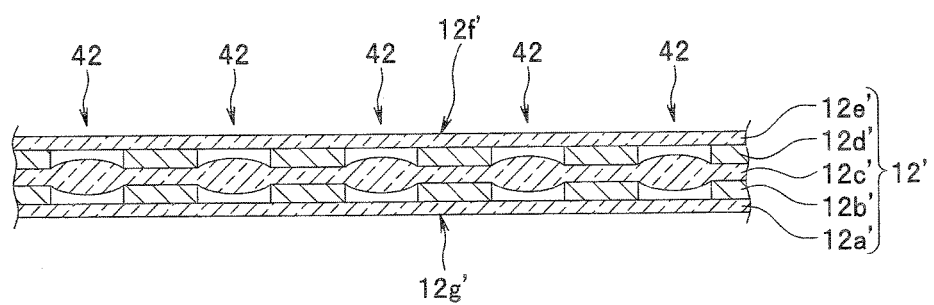
FIG. 19 is a partial sectional view of a lens unit wafer.

First, as shown in FIG. 19, plural lens wafers on which optical components are formed are bonded to form a lens unit wafer 12' including a plurality of the lens units 42. Specifically, first, the lens unit wafer 12' is formed by superimposing and bonding a lens wafer 12b' including a plurality of the spacers 42b on a lens wafer 12a' including a plurality of the flat plates 42a, superimposing and bonding a lens wafer 12c' including a plurality of the lens members 42c on the lens wafer 12b', superimposing and bonding a lens wafer 12d' including a plurality of the stops 42d on the lens wafer 12c', and superimposing and bonding a lens wafer 12e' including a plurality of the flat plates 42e on the lens wafer 12d'. As a result, a plurality of the lens units 42 including the flat plates 42a, the spacers 42b, the lens members 42c, the stops 42d, and the flat plates 42e are formed on the lens unit wafer 12'.

The lens wafers 12a' to 12d' are bonded such that transparent sections of the flat plates 42a and 42e, the through holes of the spacers 42b and the stops 42d, and the lenses 42c1 of the lens members 42c are respectively located on optical axes of light beams L.

Figure 20:
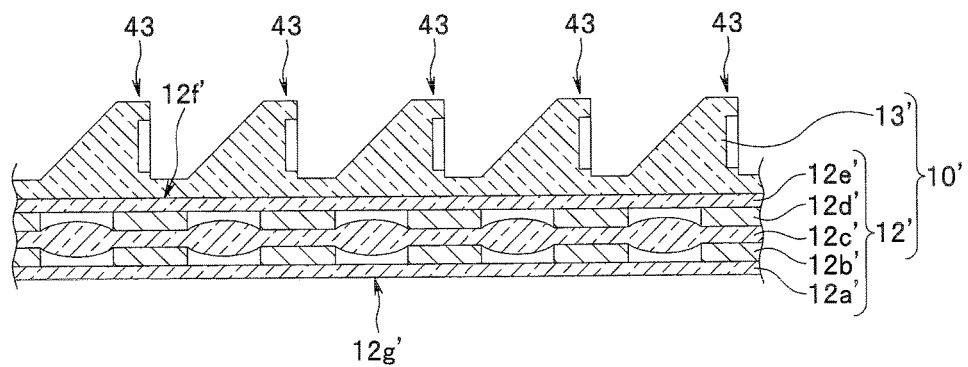
FIG. 20 is a partial sectional view of a state in which a bending optical element wafer is bonded to a first surface of the lens unit wafer shown in FIG. 19 to form an optical unit wafer.

Subsequently, as shown in FIG. 20, a bending optical element wafer 13' including a plurality of the bending optical elements 43 is bonded to a first surface 12f forming an emission surface of the light beam L of the lens unit wafer 12', specifically, an outer surface of the lens wafer 12e' such that the bending optical elements 43 are respectively opposed to the lens units 42 and incident surfaces 43c of the bending optical elements 43 are set in contact with the lens units 42. An optical unit wafer 10' including a plurality of the optical units 41 is formed.

Figure 21:
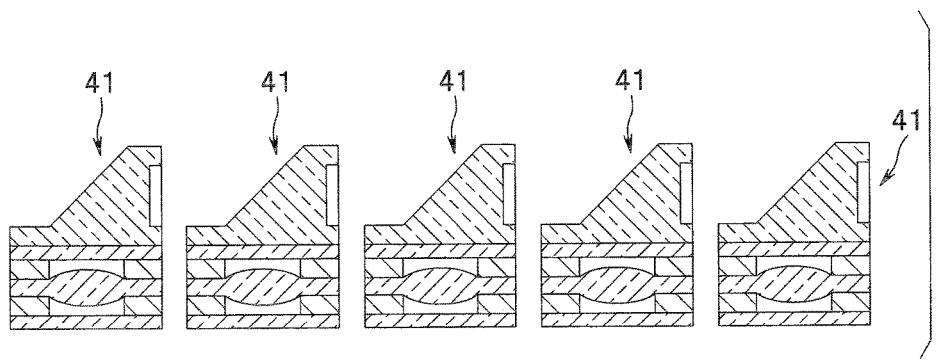
FIG. 21 is a partial sectional view of a state in which plural optical units are individualized from the optical unit wafer shown in FIG. 20.

Subsequently, as shown in FIG. 21, when the optical unit wafer 10' is separated and individualized for each of the lens units 42 and the bending optical elements 43, i.e., for each of the optical units 41, a plurality of the optical units 41 shown in FIGS. 15 and 16 are manufactured.

Finally, when the image pickup unit 45 is manufactured, as shown in FIG. 18, the solid-state image pickup devices 44 are respectively aligned and adjusted and bonded to the emission surfaces 43a of the bending optical elements 43 of the individualized optical units 41.

Specifically, the solid-state image pickup devices 44 are respectively bonded to the emission surfaces 43a in positions where spaces are formed between the light receiving sections 44a and the optical surfaces 43dt and the light receiving sections 44a receive the light beams L emitted from the optical surfaces 43dt. As a result, a plurality of the image pickup units 45 shown in FIGS. 17 and 18 are manufactured.

With such a configuration, since the solid-state image pickup device 44 is individually bonded, work efficiency falls from that in the first embodiment. Otherwise, effects same as those in the first embodiment can be obtained. Besides, the solid-state image pickup device 44 is joined to the emission surface 43a of the bending optical element 43 with a space formed on the light receiving section 44a of the solid-state image pickup device 44. Therefore, the solid-state image pickup device 44 can be formed without spoiling an effect of a microlens used for improving the performance of the image pickup unit 45. Since the bending optical element 43 is arranged on the solid-state image pickup device 44, a degree of freedom in optical design is improved. Compared with the first embodiment, the image pickup unit 45 can be formed low in height.

The optical unit or the image pickup unit explained in the first and second embodiments is provided in, for example, an endoscope.

Figure 22:
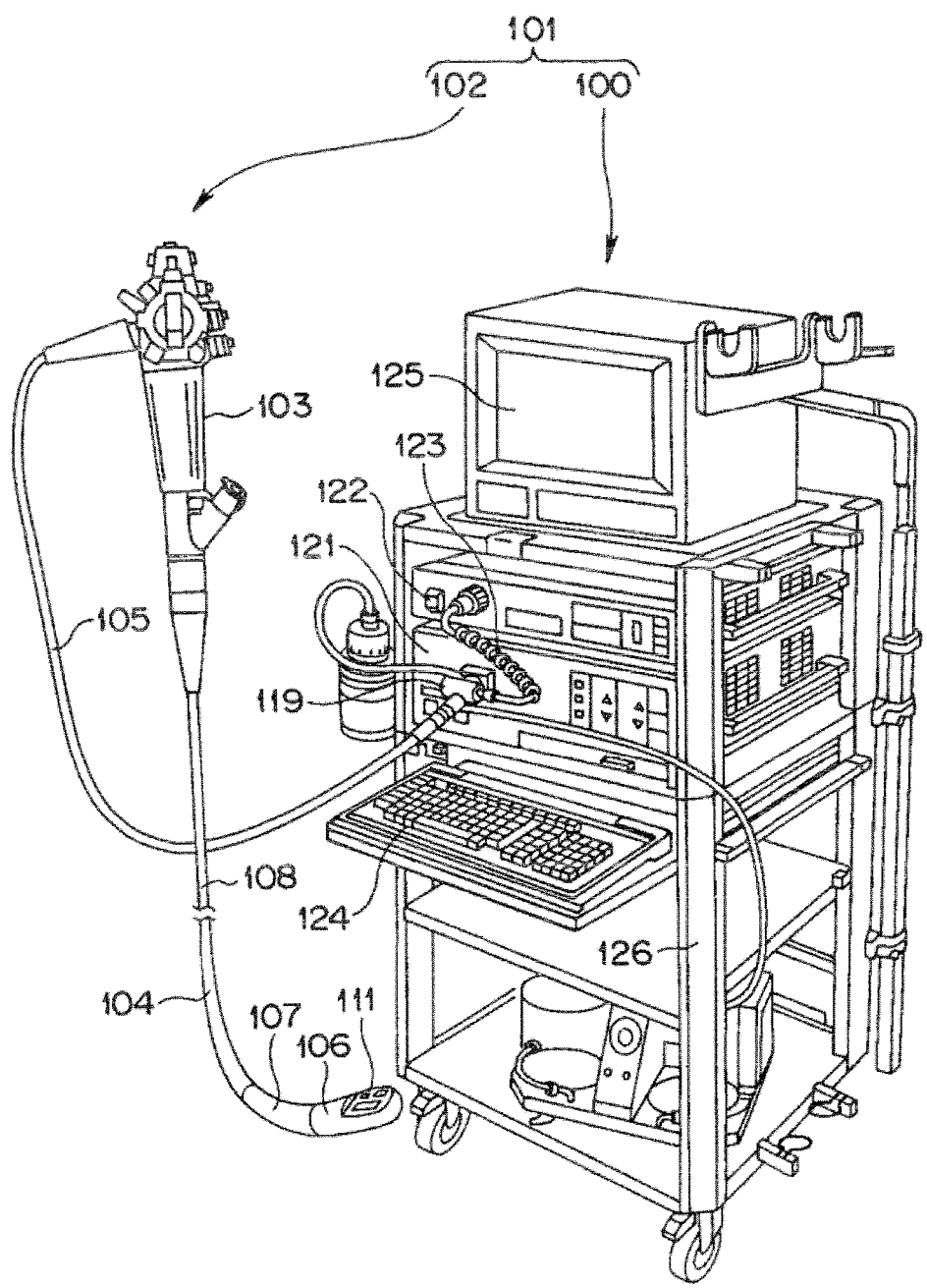
FIG. 22 is a perspective view of an endoscope apparatus including an endoscope provided with an optical unit or an image pickup unit.

As shown in FIG. 22, an endoscope apparatus 101 includes an endoscope 102 and a peripheral apparatus 100. A main section of the endoscope 102 includes an operation section 103, an insertion section 104, and a universal cord 105.

A main section of the peripheral apparatus 100 includes a light source device 121, a video processor 122, a connection cable 123, a keyboard 124, and a monitor 125 arranged on a rack 126. The endoscope 102 and the peripheral apparatus 100 having such configurations are connected to each other by a connector 119.

The insertion section 104 of the endoscope 102 includes a distal end portion 106, a bending portion 107, and a flexible tube portion 108. An object lens 111 is disposed on a side surface of the distal end portion 106. The image pickup unit 5 or the image pickup unit 45 is incorporated in the distal end portion 106.

The connector 119 is provided at the distal end of the universal cord 105 of the endoscope 102. The connector 119 is connected to the light source device 121 of the peripheral apparatus 100. A not-shown light guide cap forming an end of a not-shown light guide, an electric contact section to which an end of a not-shown image pickup cable is connected, and the like are disposed in the connector 119.

The image pickup cable is inserted from the solid-state image pickup device 4 or the solid-state image pickup device 44 in the distal end portion 106 to the electric contact section in the connector 119 through the insertion section 104, the operation section 103, and the universal cord 105. The image pickup cable transmits an electric signal of an image picked up by the solid-state image pickup device 4 or the solid-state image pickup device 44 to the video processor 122.

As explained above, if the optical unit or the image pickup unit explained in the first and second embodiments is provided in the distal end portion of the insertion section of the endoscope, the distal end portion can be further reduced in diameter.

The optical unit or the image pickup unit explained in the first and second embodiments may be applied not only to the endoscope but also to a cellular phone with camera and a digital camera.

As explained above, according to the present invention illustrated in the first and second embodiments, it is possible to reduce work for adjusting an angle of deviation and centering of an optical system in an optical unit. Further, it is possible to provide a manufacturing method for an optical unit and a manufacturing method for an image pickup unit that can reduce work for adjusting an angle of deviation and centering of an optical system in an optical unit and efficiently manufacture an optical unit or an image pickup unit and provide an optical unit and an image pickup unit manufactured by the manufacturing methods.

In other words, since an optical unit or an image pickup unit is formed at a wafer level, focus adjustment is made unnecessary by adjusting and managing the thickness of a wafer forming the optical unit or the image pickup unit. Further, accurate alignment can be easily performed by using a wafer process. Therefore, work for adjusting an angle of deviation, centering, and the like of an optical system in the optical unit is substantially reduced and a large number of optical units or image pickup units can be collectively formed. Therefore, it is possible to realize high yield and low cost.

The present invention illustrated in the first and second embodiments are as explained below.

(1) A manufacturing method for an optical unit including:
a step of bonding plural lens wafers, on which optical components are formed, and forming a lens unit wafer including plural lens units;
a step of bonding a bending optical element wafer including plural bending optical elements to a first surface of the lens unit wafer such that the plural bending optical elements are respectively opposed to the plural lens units and forming an optical unit wafer; and a step of separating and individualizing the optical unit wafer for each of the lens units and the bending optical elements and manufacturing plural optical units.

(2) A manufacturing method for an image pickup unit including:

a step of bonding plural lens wafers, on which optical components are formed, and forming a lens unit wafer including plural lens units;

a step of bonding a bending optical element wafer including plural bending optical elements to a first surface of the lens unit wafer such that the plural bending optical elements are respectively opposed to the plural lens units and forming an optical unit wafer;

a step of bonding a sensor wafer including plural solid-state image pickup devices to a second surface opposed to the first surface of the lens unit wafer in the optical unit wafer such that the plural solid-state image pickup devices are respectively opposed to the plural lens units and forming an image pickup unit wafer; and a step of separating and individualizing the image pickup unit wafer for each of the lens units, the bending optical elements, and the solid-state image pickup devices and manufacturing plural image pickup units.

(3) The manufacturing method for an image pickup unit according to (2) above, wherein the first surface of the lens unit wafer forms incident surfaces of light beams on the respective lens units, and the step of forming an image pickup unit wafer is bonding the sensor wafer to the second surface, which forms emission surfaces of light beams from the respective lens units of the lens unit wafer, in positions where light receiving sections of the respective solid-stage image pickup devices receive light beams emitted from the respective lens units.

(4) A manufacturing method for an image pickup unit including:

a step of bonding plural lens wafers, on which optical components are formed, and forming a lens unit wafer including plural lens units;

a step of bonding a bending optical element wafer including plural bending optical elements to a first surface of the lens unit wafer such that the plural bending optical elements are respectively opposed to the plural lens units and forming an optical unit wafer;

a step of separating and individualizing the optical unit wafer for each of the lens units and the bending optical elements and manufacturing plural optical units; and a step of respectively bonding solid-state image pickup devices to emission surfaces of light beams of the bending optical elements of the respective optical units.

(5) The manufacturing method for an image pickup unit according to (4) above, wherein recesses are respectively formed in the emission surfaces of the respective bending optical elements and optical surfaces are respectively formed on bottom surfaces of the recesses, and the step of bonding solid-stage image pickup devices is bonding the solid-state image pickup devices in positions where spaces are formed between the respective light receiving section of the solid-state image pickup devices and the optical surfaces of the bending optical elements and the light receiving sections receive light beams emitted from the respective optical surfaces.

(6) The manufacturing method for an image pickup unit according to (4) or (5) above, wherein the first surface of the lens unit wafer forms emission surfaces of light beams from the respective lens units, and the step of forming an optical unit wafer is bonding the bending optical element wafer to the emission surfaces of the lens unit wafer.

(7) An optical unit manufactured by the manufacturing method for an optical unit according to (1) above.

(8) An image pickup unit manufactured by the manufacturing method for an image pickup unit according to any one of (2) to (6) described above.

(9) An endoscope including the optical unit according to (7) above.

(10) An endoscope including the image pickup unit according to (8) above.

Third Embodiment

Figure 23:
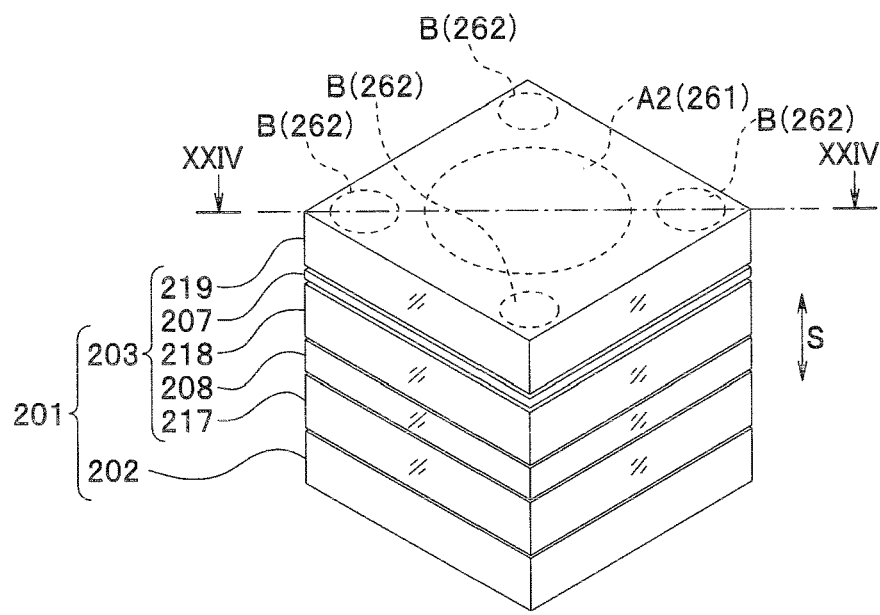
FIG. 23 is a perspective view of an image pickup unit according to a third embodiment of the present invention.
Figure 24:
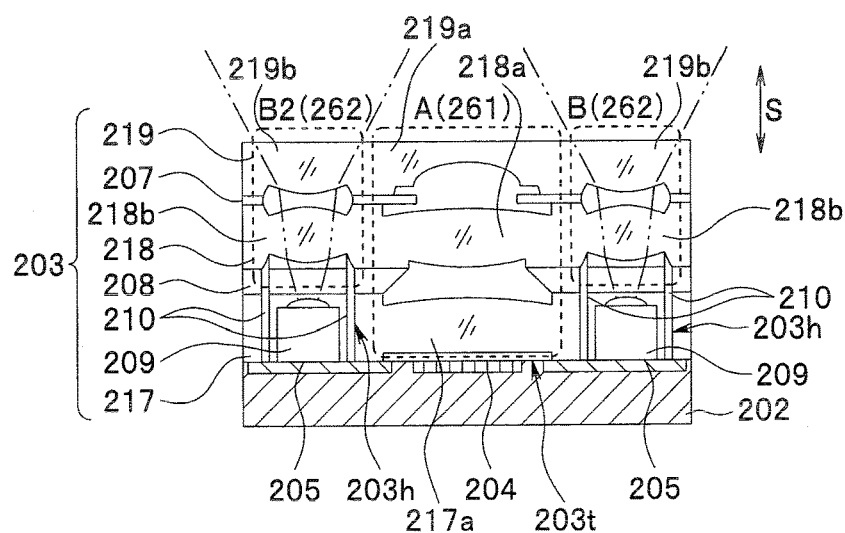
FIG. 24 is a sectional view of the image pickup unit taken along XXIV-XXIV line in FIG. 23.

An optical unit and an image pickup unit according to a third embodiment of the present invention are explained below. As shown in FIGS. 23 and 24, a main section of an image pickup unit 201 according to the present embodiment includes an image pickup device 202 and an optical unit 203.

A main section of the optical unit 203 includes a flat plate 217 as an optical component, a spacer member 208 as an optical component bonded on the flat plate 217, a flat plate 218 as an optical component bonded on the spacer member 208, a stop 207 as an optical component bonded on the flat plate 218, and a flat plate 219 as an optical component bonded on the stop 207. In other words, the optical unit 203 is formed as a laminated body formed by bonding the plural optical components 217 to 219, 207, and 208.

The stop 207 may be provided between the flat plate 217 and the flat plate 218. The spacer member 208 may be provided between the flat plate 218 and the flat plate 219. Further, the spacer member 208 does not have to be provided.

The flat plate 217 has an image pickup lens 217a in a first area 261 in a state of plan view from above of the optical unit 203, for example, the center area. The flat plate 217 is formed of a transparent member, for example, glass.

The flat plate 218 has an image pickup lens 218a in the first area 261 and has, for example, four illumination lenses 218b in second areas 262 that avoid the first area 261 in the state of plan view from above of the optical unit 203, for example, a peripheral area of the first area 261. The flat plate 218 is formed of a transparent member, for example, glass. The second areas 262 are areas other than an area where a light beam from a subject passes in the optical unit 203. Specifically, the center area in the state of plan view from above of the optical unit 203 is the first area 261 having a substantially circular shape. Areas other than the first area 261 are the second areas 262. When the state of plan view from above of the optical unit 203 is a rectangular shape, it is desirable that the illumination lenses 218b are respectively arranged, in particular, at four corners in the second areas 262. It goes without saying that only one illumination lens 218b may be provided.

The flat plate 219 has an image pickup lens 219a in the first area 261 and has, for example, four illumination lenses 219b in the second areas 262. The flat plate 219 is made of a transparent member, for example, glass. The image pickup lenses 217a to 219a are provided to be opposed to one another in a laminating direction S of the optical components 217 to 219, 207, and 208 in the first area 261. The illumination lenses 218b and 219b are provided to be opposed to one another in the laminating direction S in the second areas 262.

Specifically, in the optical unit 203, an image pickup optical section A having the image pickup lenses 217a, 218a, and 219a is formed along the laminating direction S in the first area 261. Illumination optical sections B having the illumination lenses 218b and 219b are formed along the laminating direction S in the second areas 262.

The flat plates 217 to 219 may be formed of transparent resin or a composite member of the transparent resin and the glass without being limited to be formed of glass.

The spacer member 208 sets a space in the laminating direction S between the flat plate 217 and the flat plate 218 to an arbitrary dimension. The spacer member 208 is formed of a glass plate or a resin sheet. The stop 207 decides the brightness (F number) of light made incident on the image pickup lenses 217a to 219a and blocks an unnecessary ray made incident on the image pickup optical section A. The stop 207 is formed of a black resin sheet or metal plate.

As shown in FIG. 24, in the second areas 262 of the optical unit 203, first recesses 203h are formed in the flat plate 217, the spacer member 208, and the flat plate 218 from a bottom surface 203t of the optical unit 203 along the laminating direction S.

The image pickup device 202 including, for example, a CMOS semiconductor device is bonded to the bottom surface 203t of the optical unit 203 to be integral with the optical unit 203. Specifically, the image pickup device 202 has an image pickup section 204 and first peripheral circuit sections 205 amounted with light emitting elements 209 including, for example, white LEDs. The image pickup device 202 is bonded to the bottom surface 203t of the optical unit 203 such that the image pickup section 204 is located in the first area 261, the first peripheral circuit sections 205 and the light emitting elements 209 are located in the second areas 262, and the light emitting elements 209 are located in the first recesses 203h.

Light blocking members 210 that prevent illumination light beams irradiated from the light emitting elements 209 from being made incident on the image pickup optical section A is provided in the circumferential surface of the first recesses 203h. Since the incidence of the illumination light beams on the image pickup optical section A is eliminated by the light blocking members 210, the image pickup section 204 can acquire a high-definition image.

The illumination light beams irradiated from the light emitting elements 209 are evenly expanded and irradiated to a subject in the illumination lenses 218b and 219b in the illumination optical sections B. Light emitting operation of the light emitting elements 209 is controlled by a not-shown control section outside the image pickup unit 201 in synchronization with image pickup operation of the image pickup section 204.

As shown in FIG. 23, in the present embodiment, an external shape of the image pickup device 202 and an external shape of the optical unit 203 are the same. This is because, when the image pickup unit 201 is manufactured, plural lens wafers, i.e., a lens wafer including the flat plate 217, a lens wafer including the spacer member 208, a lens wafer including the flat plate 218, a lens wafer including the stop 207, and a lens wafer including the flat plate 219 are bonded and laminated to form an optical unit wafer, a sensor wafer including the image pickup device 202 is bonded to the optical unit wafer to form an image pickup unit wafer, and then the image pickup unit wafer is sliced and divided by, for example, dicing to manufacture the image pickup unit 201.

In FIG. 23, an external shape of the image pickup unit 201 is shown as a square shape. However, the external shape of the image pickup unit 201 may be a polygonal shape such as a hexagonal shape.

After the optical unit 203 is separated from the optical unit wafer, the image pickup unit 201 may be formed by bonding the image pickup device 202 separated from the sensor wafer to the optical unit 203. Further, after the image pickup device 202 is bonded to the optical unit wafer, the image pickup unit 201 may be formed by separating the image pickup device 202 or, after the optical unit 203 is bonded to the sensor wafer, the image pickup unit 201 may be formed by separating the optical unit 203.

The external shapes of the optical unit 203 and the image pickup device 202 do not need to be the same. The optical unit 203 and the image pickup device 202 may be formed in different shapes.

As explained above, in the present embodiment, in the image pickup unit 201, the image pickup optical section A is formed in the first area 261 of the optical unit 203 and the illumination optical sections B are formed in the second areas 262. The image pickup section 204 is located in the first area 261. The first peripheral circuit sections 205 and the light emitting elements 209 are located in the second areas 262.

Consequently, since the areas other than the image pickup optical section A can be used as the illumination optical sections B, it is possible to combine illumination functions to improve the functions without increasing an image pickup unit in size. When the image pickup unit is provided at, for example, an insertion section distal end of an endoscope, an insertion section distal end portion can be reduced in size. When the image pickup unit is provided in a capsule endoscope, the capsule endoscope itself can be reduced in size. Since the image pickup optical section A and the illumination optical sections B can be integrally manufactured in the optical unit 203, assembly and machining cost for the image pickup unit 201 is reduced compared with the conventional ones.

Therefore, it is possible to provide an optical unit and an image pickup unit that can effectively utilize an area other than an area where a light beam from a subject passes and realize a reduction in size.

Fourth Embodiment

An optical unit and an image pickup unit according to a fourth embodiment of the present invention are explained below. Configurations of the optical unit and the image pickup unit according to the present embodiment are different from those of the optical unit and the image pickup unit according to the third embodiment in that a lens having a rectangular shape in plan view from above is provided on the image pickup lens 217a of the flat plate 217 and that a part of the second areas 262 of the optical unit is set as a third area 263 and a radio transmitting and receiving section is provided in the third area 263. Therefore, only these differences are explained. Components same as those in the third embodiment are denoted by the same reference numerals and signs and explanation of the components is omitted.

Figure 25:
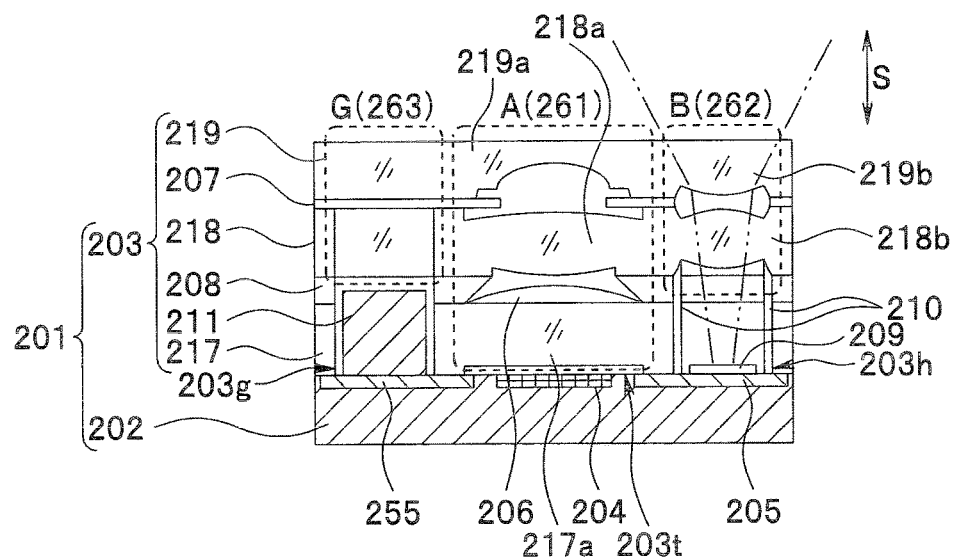
FIG. 25 is a sectional view of an image pickup unit according to a fourth embodiment of the present invention.
Figure 26:
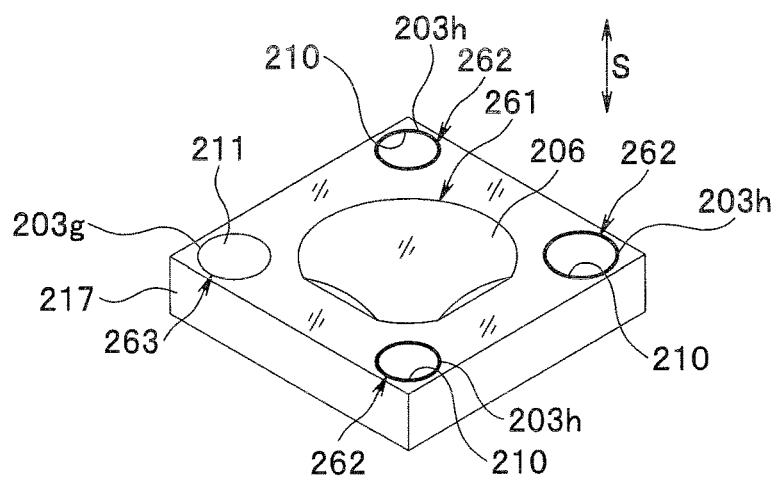
FIG. 26 is an enlarged perspective view of a flat plate shown in FIG. 25.

As shown in FIG. 25, a resin lens 206 having a curved surface on the surface of a glass plane is complexly formed on the image pickup lens 217a of the flat plate 217. As shown in FIG. 26, the resin lens 206 is formed in a shape projecting in a convex shape upward from a top surface formed in a plane of the image pickup lens 217a. A shape in plan view from above of the resin lens 206 is a rectangular shape obtained by linearly cutting off four directions of a circular shape to match a shape of the image pickup section 204 of the image pickup device 202.

This is because, since an external shape of the image pickup section 204 of the image pickup device 202 is generally a square shape, it is desirable to form an effective external shape of the resin lens 206 in a substantial square shape according to a shape of a passing area of a light beam that reaches the image pickup section 204.

The resin lens 206 may be formed on the image pickup lens 218a or on the image pickup lens 219a without being limited to be formed on the image pickup lens 217a. Further, the resin lens 206 may be formed on the illumination lenses 218b or on the illumination lenses 219b.

As shown in FIGS. 25 and 26, a radio transmitting and receiving section G is provided in the third area 263, which is a part of the second areas 262 of the optical unit 203. Because the third area 263 is a part of the second areas 262, the third area 263 is an area other than an area where a light beam from a subject passes. An area where the illumination lenses 218b are not formed in the second areas 262 is set as the third area 263. The radio transmitting and receiving section G is disposed in the third area 263.

In the third area 263 of the optical unit 203, a second recess 203g is formed in the flat plate 217, the spacer member 208, and the flat plate 218 from the bottom surface 203t of the optical unit 203 along the laminating direction S.

In the present embodiment, the image pickup device 202 includes the image pickup section 204, the first peripheral circuit sections 205 mounted with the light emitting elements 209, a radio transmitting and receiving element 211 including a transmitting and receiving antenna and a transmitting and receiving circuit formed as patterns, and a second peripheral circuit section 255 mounted with the radio transmitting and receiving element 211. The image pickup device 202 is bonded to the bottom surface 203t of the optical unit 203 such that the image pickup section 204 is located in the first area 261, the first peripheral circuit sections 205 and the light emitting elements 209 are located in the second areas 262, the light emitting elements 209 are located in the first recesses 203h, the second peripheral circuit section 255 and the radio transmitting and receiving element 211 are located in the third area 263, and the radio transmitting and receiving element 211 is located in the second recess 203g.

The radio transmitting and receiving element 211 can transmit an output signal of the image pickup device 202 to the outside by radio and control the operation of the image pickup device 202 from the outside. The radio transmitting and receiving element 211 can also transmit an identification signal peculiar to the image pickup unit 201.

Since the image pickup unit 201 according to the present embodiment includes the radio transmitting and receiving element 211, the image pickup unit 201 can be applied to, for example, a capsule endoscope for medial use.

In the present embodiment, the light emitting elements 209 located in the second areas 262 is an organic EL including a thin-film luminous element and is directly formed in the first peripheral circuit sections 205 of the image pickup device 202. Light emitting operation of the light emitting elements 209 is controlled by the first peripheral circuit sections 205 of the image pickup device 202 in synchronization with image pickup operation of the image pickup device 202.

As explained above, in the present embodiment, a part of the second areas 262 of the optical unit 203 is set as the third area 263 and the radio transmitting and receiving element 211 is provided in the third area 263.

Therefore, since areas other than the image pickup optical section A of the optical unit 203 can be used not only as the illumination optical sections B but also as the radio transmitting and receiving sections G, it is possible to realize a high-function small image pickup unit having not only an illumination function but also a radio function.

In the present embodiment, the resin lens 206 having a rectangular shape in plan view from above is formed on the image pickup lens 217a integrally with the image pickup lenses 217a. Therefore, it is possible to combine the illumination function, the radio function, and the like to improve the functions without increasing an image pickup unit in size. For example, when the image pickup unit is provided at, for example, an insertion section distal end of an endoscope, an insertion section distal end section can be reduced in size and diameter. Further, when the image pickup unit is provided in a capsule endoscope, the capsule endoscope itself can be reduced in size. Other effects of the present embodiment are the same as those in the third embodiment.

Fifth Embodiment

An optical unit and an image pickup unit according to a fifth embodiment of the present invention are explained below. Configurations of the optical unit and the image pickup unit according to the present embodiment are different from those of the optical unit and the image pickup unit according to the fourth embodiment in that the image pickup lens 218a of the flat plate 218 includes a Fresnel lens and that the image pickup lens 217a of the flat plate 217 includes an aspherical lens. Therefore, only the differences are explained. Components same as those in the fourth embodiment are denoted by the same reference numerals and signs and explanation of the components is omitted.

Figure 27:
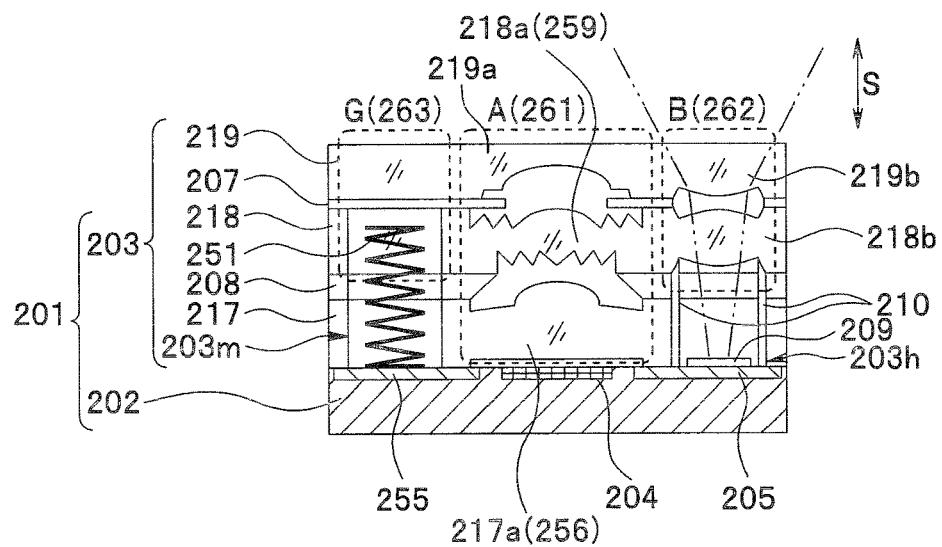
FIG. 27 is a sectional view of an image pickup unit according to a fifth embodiment of the present invention.

As shown in FIG. 27, in the present embodiment, the image pickup lens 218a includes a Fresnel lens 259. The Fresnel lens 259 is formed by molding transparent resin and is thin compared with a normal convex lens. The image pickup lens 218a may include a diffractive lens without being limited to the Fresnel lens.

The image pickup lens 217a includes an aspherical lens 256. Since the aspherical lens 256 is formed by molding glass at high temperature, a complicated lens shape is obtained compared with the normal convex lens. The illumination lenses 218b and 219b may include the Fresnel lens 259, the diffractive lens, or the aspherical lens 256.

The radio transmitting and receiving section G is provided in the third area 263 of the optical unit 203. In the third area 263 of the optical unit 203, a second recess 203m is formed in the flat plate 217, the spacer member 208, and the flat plate 218 from the bottom surface 203t of the optical unit 203 along the laminating direction S.

In the present embodiment, the image pickup device 202 includes the image pickup section 204, the first peripheral circuit sections 205 mounted with the light emitting elements 209 including, for example, white LEDs, a radio transmitting and receiving element 251 including a coil-like transmitting and receiving antenna and a transmitting and receiving circuit, and the second peripheral circuit section 255 mounted with the radio transmitting and receiving element 251. The image pickup device 202 is bonded to the bottom surface 203t of the optical unit 203 such that the image pickup section 204 is located in the first area 261, the first peripheral circuit sections 205 and the light emitting elements 209 are located in the second areas 262, the light emitting elements 209 are located in the first recesses 203h, the second peripheral circuit section 255 and the radio transmitting and receiving element 251 are located in the third area 263, and the radio transmitting and receiving element 251 is located in the second recess 203m.

The radio transmitting and receiving element 251 can transmit an output signal of the image pickup device 202 to the outside by radio and control the operation of the image pickup device 202 from the outside. The radio transmitting and receiving element 251 can also transmit an identification signal peculiar to the image pickup unit 201.

In the present embodiment, as in the second embodiment, the radio transmitting and receiving element 251 transmits a signal outputted from the second peripheral circuit section 255 of the image pickup device 202 to the outside and receives a signal from the outside and transmits the signal to the second peripheral circuit section 255.

Since the image pickup unit 201 having the configuration explained above includes the radio transmitting and receiving element 251, the image pickup unit 201 can be applied to, for example, a capsule endoscope for medical use.

In the present embodiment, the image pickup lens 218a includes the Fresnel lens 259 and the image pickup lens 217a includes the aspherical lens 256. Consequently, optical path length in the image pickup optical section A can be set shorter than that in the fourth embodiment. Therefore, the image pickup unit 201 can be further reduced in size and the performance of the image pickup optical section A can be further improved. Other effects are the same as those in the fourth embodiment.

Figure 28:
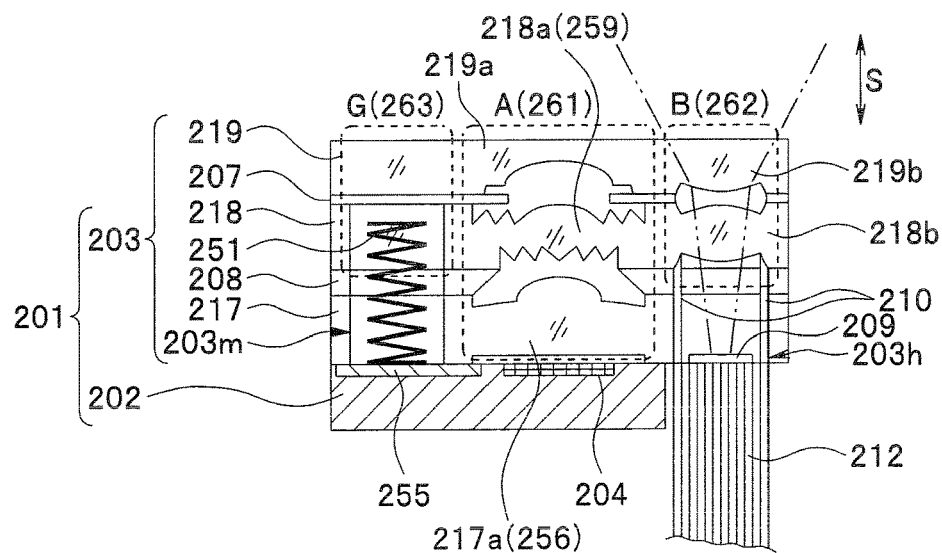
FIG. 28 is a sectional view of a configuration of a modification of the image pickup unit according to the fifth embodiment.

A modification of the present embodiment is explained with reference to FIG. 28. In the present embodiment explained above, the light emitting elements 209 are located in the second recesses 203h in the illumination optical sections B. However, the present invention is not limited to this. As shown in FIG. 28, light guides 212 may be arranged instead of the light emitting elements 209 in the illumination optical sections B. Not-shown lamps are arranged on proximal end sides of the light guides 212. The light guides 212 transmit light beams emitted according to light emission of the lamps to the image pickup unit 201 as illumination light beams. The transmitted illumination light beams are expanded and irradiated to a subject in the illumination optical sections B.

In the present configuration, as shown in FIG. 28, an external shape of the image pickup device 202 is set smaller than that of the optical unit 203 to avoid the light guides 212. However, not-shown through holes for insertion are formed in the image pickup device 202 or four corners of the image pickup device 202 are chamfered, whereby distal ends of the light guides 212 are arranged in positions facing the illumination optical sections B.

In the present embodiment, the radio transmitting and receiving element 251 is provided in the third area 263. However, the present invention is not limited to this. A sensor such as an acceleration sensor, a magnetic sensor, or a GPS, a motor, or an actuator such as a piezoelectric element may be arranged in the third area 263. The same holds true in the fourth embodiment.

The optical unit or the image pickup unit explained in the third to fifth embodiments is able to be provided in, for example, the endoscope shown in FIG. 22. An endoscope, for example, an endoscope for oblique view including the optical unit or the image pickup unit explained in the third to fifth embodiments at a distal end portion of an insertion section has a small diameter at the distal end portion.

The optical unit or the image pickup unit explained in the third to fifth embodiments may be provided in a capsule endoscope for medical use or may be applied not only to the endoscope but also to a cellular phone with camera and a digital camera.

As explained above, according to the present invention illustrated by the third to fifth embodiments, it is possible to provide an optical unit, an image pickup unit, a manufacturing method for an optical unit, and a manufacturing method for an image pickup unit that can effectively utilize an area other than an area where a light beam from a subject passes and realize a reduction in size.

Specifically, the present invention illustrated in the third to fifth embodiments is as explained below.

(1) An optical unit including a laminated body including:

an image pickup optical section formed to have, in a state of plan view from above of the laminated body formed by bonding plural optical components, an image pickup lens along a laminating direction of the optical components in a first area of the laminated body; and an illumination optical section formed to have, in the state of plan view from above of the laminated body, an illumination lens along the laminating direction in a second area set to avoid the image pickup optical section.

(2) The optical unit according to (1) above, wherein the image pickup lens and the illumination lens include plural lenses, and a Fresnel lens or a diffractive lens is provided in at least one of at least a part of the image pickup lens and at least a part of the illumination lens.

(3) The optical unit according to (1) above, wherein at least a part of the image pickup lens has a rectangular external shape in plan view from above.

(4) The optical unit according to any one of (1) to (3) above further including a radio transmitting and receiving section in a third area that forms a part of the second area in the state of plan view from above of the laminated body.

(5) An image pickup unit including an optical unit and an image pickup device mounted with the optical unit including:

an image pickup optical section formed to have, in a state of plan view from above of the optical unit including a laminated body formed by bonding plural optical components, an image pickup lens along a laminating direction of the optical components in a first area of the optical unit;

an illumination optical section formed to have, in the state of plan view from above of the optical unit, an illumination lens along the laminating direction in a second area set to avoid the image pickup optical section;

a first recess drilled along the laminating direction from a bottom surface of the optical unit in the second area of the optical unit; and the image pickup device having an image pickup section and a first peripheral circuit section, in which a light emitting element is provided, and bonded to the bottom surface of the optical unit such that the image pickup section is located in the first area, the first peripheral circuit section and the light emitting element are located in the second area, and the light emitting element is located in the first recess.

(6) The image pickup unit according to (5) above, wherein a light blocking member is provided on a circumferential surface of the first recess.

(7) The image pickup unit according to (5) or (6) above further including a radio transmitting and receiving section in a third area that forms a part of the second area in the state of plan view from above of the optical unit.

(8) The image pickup unit according to (7) above further including:

a second recess drilled along the laminating direction from the bottom surface of the optical unit in the third area of the optical unit;

the image pickup device including the image pickup section, the first peripheral circuit section, in which the light emitting element is provided, and a second peripheral circuit section, in which a radio transmitting and receiving element is provided, and bonded to the bottom surface of the optical unit such that the image pickup section is located in the first area, the first peripheral circuit section and the light emitting element are located in the second area and the light emitting element is located in the first recess, and the second peripheral circuit section and the radio transmitting and receiving element are located in the third area and the radio transmitting and receiving element is located in the second recess.

(9) The image pickup unit according to any one of (5) to (8) above, wherein the image pickup lens and the illumination lens include plural lenses; and a Fresnel lens or a diffractive lens is used in at least one of at least a part of the image pickup lens and at least a part of the illumination lens.

(10) The image pickup unit according to any one of (5) to (9) above, wherein the image pickup lens and the illumination lens include plural lenses; and at least one of at least a part of the image pickup lens and at least a part of the illumination lens has a rectangular external shape in plan view from above.

(11) An endoscope including the optical unit according to any one of (1) to (4) above.

(12) An endoscope including the image pickup unit according to any one of (5) to (10) above.

Having described the preferred embodiments of the invention referring to the accompanying drawings, it should be understood that the present invention is not limited to those precise embodiments and various changes and modifications thereof could be made by one skilled in the art without departing from the spirit or scope of the invention as defined in the appended claims.

What is claimed is:

1. A method comprising:
    bonding lens wafers comprising optical components to form a lens unit wafer comprising lens units;
    bonding a bending optical element wafer comprising bending optical elements to a first surface of the lens unit wafer to form an optical unit wafer such that the bending optical elements are respectively opposed to the lens units to arrange respective inclined planes of the bending optical elements to be inclined relative to the first surface of the lens unit wafer to refract light beams emitted from the lens units towards respective emission surfaces of the bending optical elements;
    separating and individualizing the optical unit wafer for each of the lens units and the bending optical elements to manufacture optical units; and
    respectively bonding solid-state image pickup devices to the emission surfaces of the bending optical elements of the optical units.

2. The method according to claim 1, comprising:
    respectively forming recesses in the emission surfaces of the bending optical elements, wherein the emission surfaces in which the recesses are formed comprise optical surfaces; and
    respectively bonding the solid-state image pickup devices to the emission surfaces of the bending optical elements of the optical units such that a space is formed between each of light receiving sections of the respective solid-state image pickup devices and each of the optical surfaces of the bending optical elements, and the solid-state image pickup devices are arranged in positions where the light receiving sections receive respective lights emitted from the optical surfaces.

3. The method according to claim 1,
    wherein the first surface of the lens unit wafer forms emission surfaces of light beams from the respective lens units, and
    wherein forming the optical unit wafer comprises bonding the bending optical element wafer to the emission surfaces of the lens unit wafer.

4. An image pickup unit comprising one of the solid-state image pickup devices bonded to one of the optical units, manufactured with the method according to claim 1.

* * * * *